United States Patent [19]

Cherubini

[11] Patent Number: 5,015,251
[45] Date of Patent: May 14, 1991

[54] MEDICAL FASTENER STRAP

[75] Inventor: Julian H. Cherubini, Newton, Mass.

[73] Assignee: AliMed, Inc., Dedham, Mass.

[21] Appl. No.: 676,565

[22] Filed: Nov. 30, 1984

[51] Int. Cl.⁵ .............................................. A61B 17/12
[52] U.S. Cl. ............................ 606/203; 128/DIG. 15;
      24/16 R; 24/442
[58] Field of Search ....... 128/327, DIG. 15, DIG. 26,
      128/149, 133, 134, 155, 156; 604/179, 391;
      24/16 R, 204, 442, 306; 606/203

[56] References Cited

U.S. PATENT DOCUMENTS

| | | | |
|---|---|---|---|
| D. 254,214 | 2/1980 | Leary | 128/DIG. 15 |
| 1,885,007 | 10/1932 | Rosenblatt | 128/327 |
| 2,519,712 | 8/1950 | Stegeman | 128/327 |
| 3,000,384 | 9/1961 | Piers, Jr. | 128/DIG. 15 |
| 3,086,529 | 4/1963 | Munz et al. | 128/327 |
| 3,190,444 | 6/1965 | Kelson | 128/DIG. 15 X |
| 3,297,026 | 1/1967 | Van Pelt | 128/DIG. 15 X |
| 3,376,865 | 4/1968 | Gamper | 128/DIG. 15 |
| 3,535,718 | 10/1970 | Murcott | 128/DIG. 15 X |
| 3,543,977 | 12/1970 | Lockridge | 128/DIG. 15 |
| 3,586,001 | 6/1971 | Sanderson | 128/327 |
| 4,149,540 | 4/1979 | Hasslinger | 128/327 |
| 4,182,338 | 1/1980 | Stanulis | 128/327 |
| 4,273,130 | 6/1981 | Simpson | 128/327 |
| 4,384,583 | 5/1983 | Speelman et al. | 128/327 |
| 4,414,969 | 11/1983 | Heyman | 128/DIG. 15 X |
| 4,422,455 | 12/1983 | Olsen | 128/DIG. 15 X |

FOREIGN PATENT DOCUMENTS 496590 10/1953 Canada ............................ 128/327

*Primary Examiner*—Laurie K. Cranmer
*Assistant Examiner*—J. Hakomaki
*Attorney, Agent, or Firm*—Wolf, Greenfield & Sacks

[57] ABSTRACT

A medical fastener strap for engaging the body has an elongated stiff strip of resilient engaging members on one side and a mating and overlapping elongated softer strip of material on a second side carrying coacting engaging members for coacting with the first strip. The strap is wrapped about a body member and overlapped at its ends to form a Velcro-type fastener. Parallel edges of the softer strip extend over and beyond edges of the stiffer strip and are positioned adjacent the body to cushion and protect the body from the stiff strip in use.

5 Claims, 1 Drawing Sheet

MEDICAL FASTENER STRAP

BACKGROUND OF THE INVENTION

A number of straps or bands for orthotic and medical use for attachment to arms, legs and other portions of the body have long been known. Such bands are represented in the prior art by U.S. Pat. Nos. 4,088,136, 4,445,894, 3,086,529, 3,812,851, 3,782,378 and 3,878,849.

Various Velcro-type fasteners have been used for engaging ends of the straps having various combinations of layers. Depending upon the use of the straps, i.e., as anchoring devices for catheters, supporting limbs at elevated positions, EKG straps, I.V. tubes, slings, restraints, cable supports, or the like, the straps are varied in construction. In some cases prior art straps have limited adjustability to various size limbs, difficulty of attachment or fabrication or discomfort in use.

SUMMARY OF THE INVENTION

It is an object of this invention to provide a medical fastener strap useful for application to the body which is comfortable in use and avoids excessive abrasion or cutting into the skin of the body portion with which it is used and minimizes subcutaneous forces adjacent to the strip edge.

Another object of this invention is to provide a medical fastener strap in accordance with the preceding object which is highly versatile, low cost in construction and adjustable for many uses in varying sizes as desired.

Still another object of this invention is to provide a reusable, easily applied and fastened medical adjustable strap.

According to the invention a medical fastener strap suitable for comfortable use in engaging the body has a first elongated stiff strip defining an outer surface and an inner surface with elongated peripheral edges. The first elongated strip outer surface carries a plurality of resilient engaging members. A second elongated strip has an inner surface and an outer surface with elongated peripheral side edges. The second outer surface comprises a plurality of second engaging members designed and arranged to contact with the first engaging members to form a separable fastener. The second strip underlies the first strip and has extended edges forming cushioning flaps extending beyond the first strip edges to protect the underlying body member from the stiff edge of the first strip in use. The strap is wound around the body portion to overlap with the first outer surface engaging the second outer surface in separable engagement therewith. The engaging members are preferably hooks on the first strip and loops on the second strip of a conventional Velcro-type fastener device.

Preferably the strap is wound in long lengths as, for example, three feet or more. When a defined length fastener strap is wanted, a surgical scissors is used to cut the strip to the desired length.

It is a feature of this invention that the materials of the strap can be designed to be autoclavable, reusable and have desired fastening and separable properties. It is a further feature that the overlapping cushioning flaps which extend from the wider second strip parallel to the edges of the first strip curl over the extreme outer ends of the first strip and fully protect the body in use from the stiffness, roughness and cutting features that would otherwise occur with the use of a fastening member having the required stiffness to form a good Velcro-type closure.

BRIEF DESCRIPTION OF THE DRAWINGS

The above and other features, objects and advantages of the present invention will be better understood from a reading of the enclosed specification along with the accompanying drawings in which.

BRIEF DESCRIPTION OF PREFERRED EMBODIMENT

Figure 1:
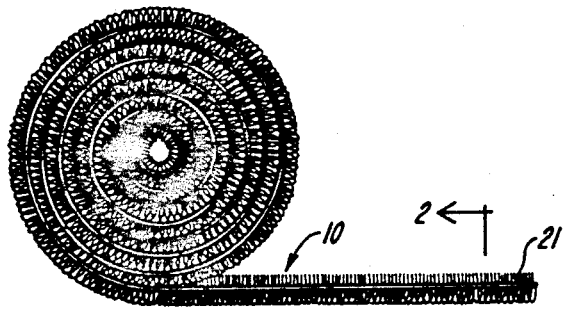
FIG. 1 shows a roll of a preferred embodiment of the fastener strip of this invention.

A multi-purpose, self-adjusting medical fastener strap in accordance with the present invention is illustrated generally at 10 in FIG. 1, rolled upon itself in a convenient storage and dispensing roll.

The strap is pliable, easily bendable and has slightly more body than an Ace bandage device. The strap 10 in roll form as shown in FIG. 1 can come in varying lengths and can be cut to size to meet any particular requirement. For example, lengths of from eight inches or thirty feet or more can be rolled in a single storage bundle.

The strap is made up of two components in the form of a first elongated stiff strip 11 extending along the elongated axis of the strap and a second elongated strip 12 forming a backing for the strip 11 and joined thereto by a suitable adhesive stitching or other fastening means.

The strip 11 has an outer surface 13, peripheral elongated side edges 14 and 15 preferably parallel to each other and an inner surface 16.

The inner surface 16 is attached to the inner surface 17 of the strip 12 which itself has parallel peripheral side edges 18 and 19 extending beyond the edges 14, 15 as will be described. The strip 12 has an outer surface 20 of second engaging members designed to be separably mated with first engaging members 21 extending from the outer surface of the strip 11.

Figure 2:
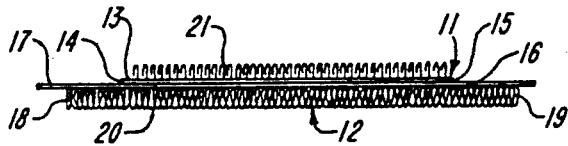
FIG. 2 is a cross section therethrough along line 2—2.
Figure 3:
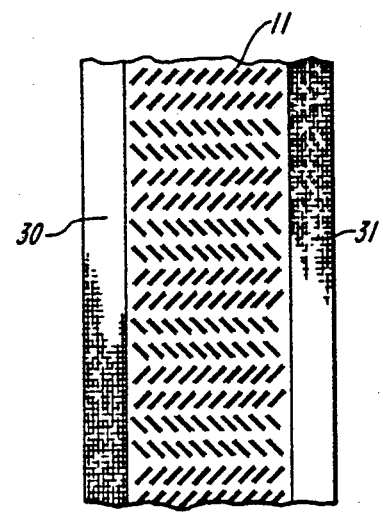
FIG. 3 is a top plan view.
Figure 5:
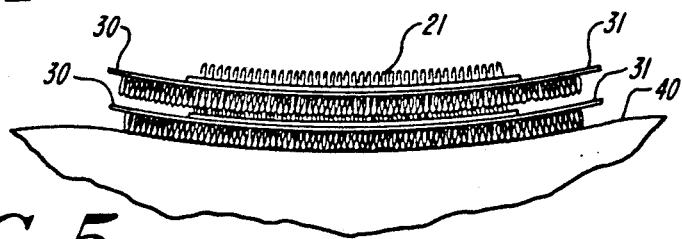
FIG. 5 is a cross section through line 5—5 of FIG. 4.

The strip 11 is preferably a Velcro or Velcro-type engaging member carrying hooks. For example, nylon hook #65 or nylon hook #80 of the Velcro type, a trademark product of Smalley & Bates Division Velcro U.S.A., Inc. of Cedar Grove, N.J., are preferred for use. Such engaging members have a nylon strip backing with hooks extending upwardly as illustrated in FIGS. 2 and 5. Nylon hook #80 has over 200 monofilament nylon hooks per inch providing for high shear or pulling strength as well as the benefit of the easy opening by peeling.

The nylon hook or other Velcro-type separable closure is adapted to mate with the outer surface 20 of the strip 12. The strip 12 can be a loop tape where the loops form the mating engaging members. Nylon loop tape 1000 or knitted loop #3302, available from Velcro U.S.A., Inc., which are respectively multi-loop nap finish soft tapes and unnapped looped material that provide high strength, high-opening closing cycle durability while retaining a soft cushioned feel can be used. Other loop materials having a soft cushioning feel can also be used.

The tape 12 extends beyond the edges of the tape 15. For example, in the preferred embodiment, the strip 15 is a one inch wide nylon hook #65 sewn or glued, as for example with Velcro liquid adhesive #40, to a one-and-a-half inch wide nylon loop tape 1000. The side flanges or flaps 30, 31 that extend beyond the edges 14 and 15 are the key portion of the present invention in the combination shown. These flap members 30, 31 bend upwardly as best shown in FIG. 5 when the tape is in use about a body limb such as an arm portion diagrammatically shown at 32. Because the flaps 30, 31 separate the edges 14 and 15 from the arm portion and particularly the bulge such as 40 shown in FIG. 5 which is separated from the lowermost portion of edge 15, a cushioning effect is provided by the flaps. This prevents the lowermost portion of edges 14 and 15 from cutting into abrading and otherwise irritating the skin and arm 32 in use when the fastener is applied. The feature also reduces subcutaneous sheer forces which can have a destructive effect on soft tissue.

Figure 4:
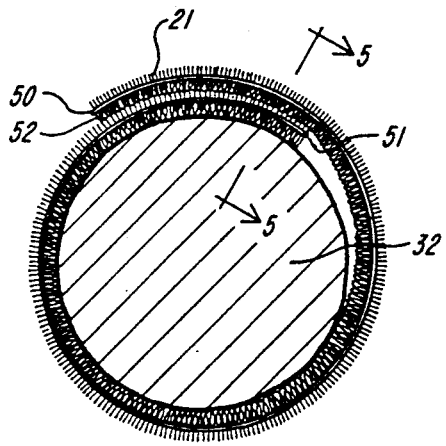
FIG. 4 is a cross section through a length of the strip of FIG. 1 wound about a body limb.

As shown in FIG. 4, lengths of the fastener strip cut to size, as desired, are applied over the limb and separably fastened as at overlapped edges 50, 51. The seal or joint formed at 52 is between the hooks 21 and loops at the surface 20 and can be quite strong assuming an overlap of at least one-half inch or more is used. The strength of the seal and separable qualities thereof can be determined by the amount of overlap as well as selection of materials as desired. In all cases, flaps 30 and 31 provide the cushioning effect desired. The exact extent of the flap portion beyond edges 14 and 15 can be varied. One-quarter inch of overlap is preferred for most applications to provide the required cushioning without unduly increasing cost or adding to the weight or bulk of the item. In some cases, the overlap portion can be thinner. It is important that the overlap portion extends adjacent the Velcro hook or stiff portions wherever it occurs.

The medical fastener strap preferably has flaps which extend out from the peripheral edges 14 and 15 a distance greater than the thickness of the strip 11. In the preferred embodiment, the strips 11 and 20 are continuous or substantially continuous throughout the axial length of the roll of material.

Preferably the materials used are autoclavable and washable and allow for quick application and release. Because Velcro type fasteners are used, i.e., hook and loop fasteners, no adhesives are needed to form the seals and patient discomfort by adhesive attachment to the skin is avoided.

The flexible tape or strip members 11 and 12 can be formed of other materials than those specifically described. Many separable fastener tape materials are known. The separable fastener member 11 can be woven or knitted or synthetic heat deformable material such as nylon, polyester and the like having resilient engaging elements upstanding from a base member. Hook-type members are preferred although the term "hook-type" as used in this specification is meant to include any flexible engaging element such as mushroom-like elements, resilient projections and the like which are readily securable in face-to-face relationship and resist forces parallel to the interfacial plane of engagement. The strip of knitted or textile material 12 can be made from nylon mutli-filament yarns constricted to have a multiplicity of loop-type filamentary engaging elements.

FIG. 4 shows only the tape wrapped about the limb 32. It is obvious that a tube can lie between the limb or the tape can act as a hanger, restraint or other device to which the limb is to be attached in any way.

While specific embodiments of the present invention have been shown and described, many variations are possible.

The dimensions and materials can vary greatly. Thus the width of the strap can be in sizes such as one-half inch to eight inches or more. While the overall thickness of each strip in the strap is small, it can vary from 0.010 to 0.25 inch or more. In all cases the overlap of flaps 30, 31 provide a cushion to protect the body, avoid irritation and physically separate the stiff strip or any irritating portion thereof from the body.

I claim:

1. A medical fastener strap suitable for comfortable use in engaging the body and comprising, a first elongated continuous stiff strip defining a first outer surface and an inner surface with elongated peripheral edges and having said outer surface carrying a plurality of resilient Velcro-type first engaging members, a second continuous elongated strip having an inner surface and an outer surface with elongated peripheral side edges, said outer surface of said second elongated continuous strip comprising a plurality of second engaging members designed and arranged to coact with said first engaging members to form a separable fastener, said second strip underlying said first strip and attached thereto having cushioning flaps with a width greater than the thickness of said first strip extending beyond said first strip edges to protect underlying body members therefrom in use, whereby said strip can be wound around a body portion to overlap with said first outer surface engaging said second outer surface in separable engagement therewith.

2. A medical fastener strap in accordance with claim 1 wherein said first engaging members are hook-type resilient engaging members and said second engaging members are corresponding loop-type engaging members with said second strip being of a softer material than said first strip.

3. A medical fastener strap in accordance with claim 2 wherein said first and second strip are adhesively united along their length.

4. A medical fastener strap in accordance with claim 1 wherein said strap is in a roll having a length of greater than three feet.

5. A method of preventing irritation to the body when an elongated strap is would thereover to press into soft tissue of the body with said strap having a first substantially continuous stiff strip carrying engaging members, said method comprising positioning a softening and cushioning substantially continuous layer to extend beyond edges of said strip and prevent contact of said strip directly with the body, said layer further acting as a means for engaging said members to form a separable fastener and reduce subcutaneous shear forces applied to the body when said means for engaging and said engaging members are brought in to engagement compressing a body portion thereunder.

* * * * *